United States Patent [19]

Chapman

[11] 4,180,526

[45] Dec. 25, 1979

[54] ALKYLATION PROCESS UTILIZING SIDE DRAW VAPOR AS HEAT SOURCE IN ISOSTRIPPER

[75] Inventor: Charles C. Chapman, Bartlesville, Okla.

[73] Assignee: Phillips Petroleum Company, Bartlesville, Okla.

[21] Appl. No.: 922,916

[22] Filed: Jul. 7, 1978

[51] Int. Cl.² .................................................. C07C 3/54
[52] U.S. Cl. ..................................... 585/719; 585/723
[58] Field of Search ..................... 260/683.48, 683.49, 260/683.62, 683.43, 683.58

[56] References Cited

U.S. PATENT DOCUMENTS

| | | | |
|---|---|---|---|
| 2,910,521 | 10/1959 | Cobb, Jr. | 260/683.48 |
| 3,763,022 | 10/1973 | Chapman | 260/683.48 |
| 3,957,901 | 5/1976 | Chapman | 260/683.43 |
| 4,115,471 | 9/1978 | Kesler | 260/683.62 |

*Primary Examiner*—George Crasanakis

[57] ABSTRACT

An olefin and isoparaffin are contacted in the presence of an acid alkylation catalyst to form an alkylate-containing alkylation effluent. The effluent is separated with the hydrocarbon phase passing to a prefractionation zone. A side stream from the prefractionation zone is passed in indirect heat exchange relationship with an interheater of an isostripper thereby providing a majority of the heat necessary to reboil the isostripper.

6 Claims, 1 Drawing Figure

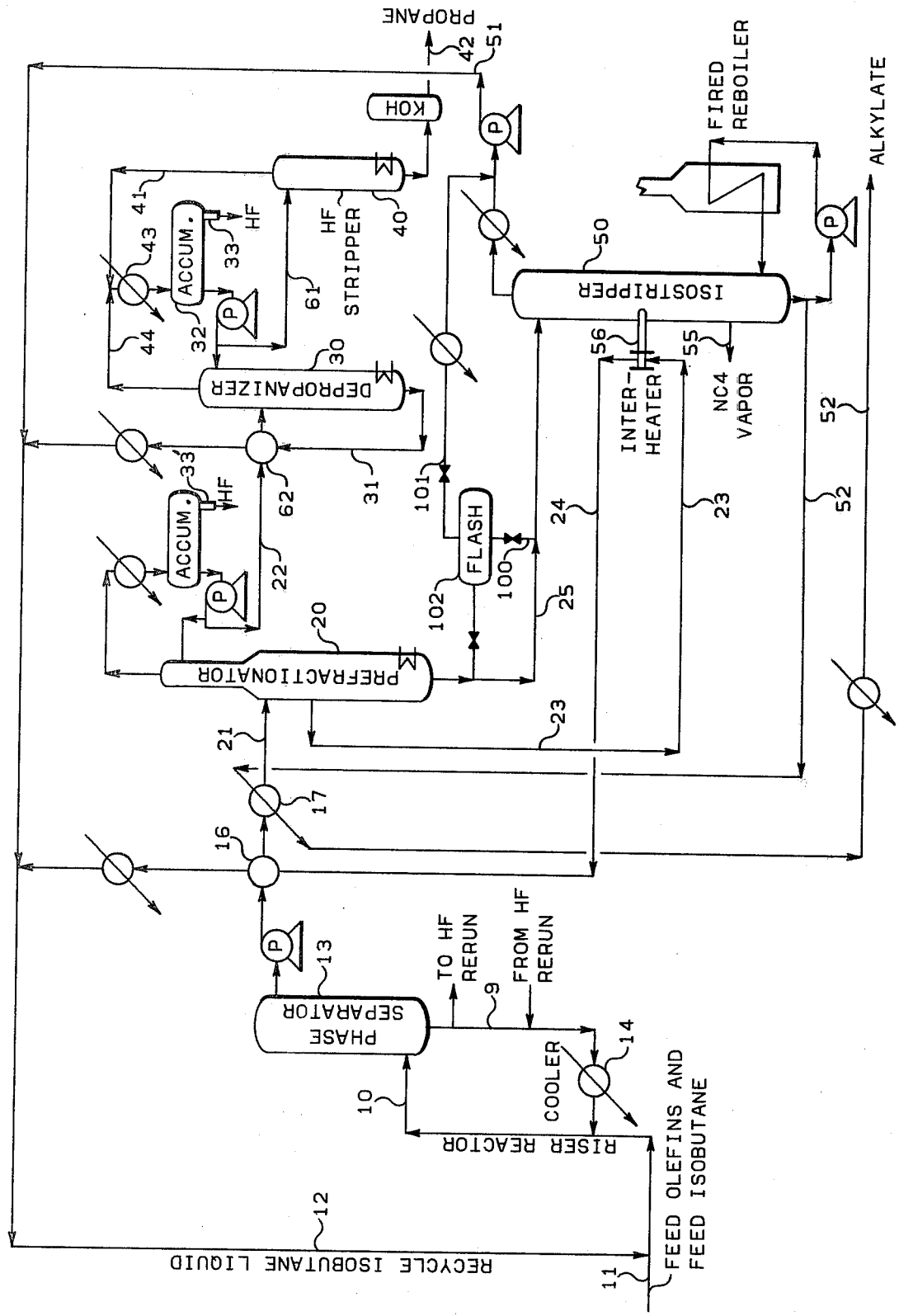

ALKYLATION PROCESS UTILIZING SIDE DRAW VAPOR AS HEAT SOURCE IN ISOSTRIPPER

BACKGROUND OF THE INVENTION

This invention relates to a process for alkylating an alkylatable isoparaffinic hydrocarbon with olefinic hydrocarbons. In another aspect, this invention relates to a process for the alkylation of isoparaffins with olefins in the presence of a hydrofluoric acid catalyst. In yet another aspect, this invention relates to an alkylation process wherein energy is conserved through the use of waste heat available in a stream obtained from the prefractionation zone. In still another aspect, this invention relates to an alkylation process wherein a side draw stream from the prefractionation zone is passed in indirect heat exchange relationship with the interheater of an isostripper. In another aspect, this invention relates to an alkylation process wherein the bottoms from the prefractionation zone is flashed prior to being charged to the isostripper thereby reducing the amount of liquid that needs to be heated and vaporized in the isostripper. In another aspect, this invention further relates to an alkylation process in which the majority of heat needed by an isostripper is supplied by a side draw stream taken from the prefractionation zone.

Alkylation of isoparaffinic hydorcarbons, such as isobutane, isopentane, and the like, with olefinic hydrocarbons such as propylene, butylene, amylenes, and the like is well known as a commercially important method for producing gasoline boiling range hydrocarbons. Generally, the alkylation of isoparaffins with olefins is accomplished by contacting the reactants with an acid-acting catalyst, settling the mixture to separate the catalyst from hydrocarbons, and further separating the hydrocarbon stream into its various components including the alkylate product. The alkylate is typically a mixture of isomers of heptane, octane, etc., with the exact composition depending upon the isoparaffin and olefin reactants used. Various types of catalysts have been utilized in this reaction, including sulfuric acid, hydrofluoric acid, phosphoric acid, certain halosulfonic acids, and aluminum chloride. The preferred catalyst is hydrofluoric acid, however, because of the relative ease with which it can be used and reused and because of the superior quality of the alkylate that is produced.

The energy requirements for heating the various separation zones and streams of an alkylation process are great and it would be desirable, therefore, to maintain the energy requirements of the alkylation process at a minimum level. This is particularly important where energy is valuable and the products for generating the energy are in relatively short supply and expensive.

Accordingly, it is an object of this invention to provide an improved alkylation process which conserves energy by utilizing the available heat in the process in a more efficient manner.

Another object of this invention is to provide an alkylation process which minimizes the energy requirements.

It is another object of this invention to provide an alkylation process wherein the majority of heat required by the isostripper is supplied by the waste heat available in a side draw stream from the prefractionation zone.

Another object of this invention is to provide an improved alkylation process in which the isostripper requires little, if any, additional heat energy than that obtained from an interheater which is heated by waste heat available in the process.

Other objects, aspects, and the several advantages of this invention will be apparent to those skilled in the art upon a study of the disclosure, the appended claims, and the drawing.

SUMMARY OF THE INVENTION

This invention relates to an alkylation system wherein a side draw stream is removed from the prefractionation zone and used for interheating the isostripper. Most of the heat required for the isostripper can come from the interheater. The use of the waste heat in the side draw stream to heat the interheater can result in substantial heat savings as it reduces the amount of heat necessary from outside of the process to heat the isostripper.

Additional heat savings can be realized upon using the side draw stream from the prefractionation zone and the bottoms from the isostripper as heat exchange mediums for preheating a feed stream to a tower, e.g., the feed stream to a prefractonation zone.

In another embodiment of the invention, the load, and thereby the amount of heat needed by the isostripper, can be reduced by flashing the bottoms fraction of the prefractionation zone with the flashed vapor being recycled to alkylation in the remaining liquid or residue being charged to the isostripper as feed. The flashing of the bottoms fraction removes some of the isoparaffin as vapor and thereby reduces the amount of isoparaffin being fed to the isostripper that needs to be heated, vaporized, and collected as overhead.

BRIEF DESCRIPTION OF THE DRAWING

The FIGURE depicts several embodiments of the invention including the taking of a side draw stream from the prefractionator and passing it in indirect heat exchange relationship with the interheater of the isostripper.

DETAILED DESCRIPTION OF THE INVENTION

This invention relates to an alkylation process involving the contacting of an olefin and isoparaffin in the presence of an acid alkylation catalyst under such alkylation conditions as to form an alkylate containing alkylation effluent. The effluent is passed to a phase separation zone and allowed to separate into a hydrocarbon phase and an acid catalyst phase. The hydrocarbon phase is then passed to a prefractionation zone wherein the hydrocarbon phase is separated into at least three fractions with one fraction being an overhead vapor fraction, another being a bottoms liquid fraction, and the third being a side draw vapor stream. The side draw vapor stream taken from the prefractionation zone is passed in indirect heat exchange relationship with the interheater of an isostripper in order to provide the majority of heat energy required by the isostripper. Once passed in indirect heat exchange relationship with the isostripper, the vapor stream can then be recycled to alkylation. The overhead fraction from the prefractionation zone can be charged to a depropanizer with the bottoms fraction of the prefractionation zone being charged to an isostripper as feed.

The prefractionation zone is preferably operated at high pressure in order to obtain a very high temperature side stream therefrom. The higher the temperature of the vapor side draw stream, the more heat it can furnish to the isostripper thereby reducing the amount of independent heat energy necessary to reboil the isostripper. The isostripper, however, is preferably run at a low pressure as opposed to the high pressure of the prefractionator.

Additional heat savings can be realized by further utilizing the waste heat available in the vapor side draw stream from the prefractionation zone as well as the heat available in the bottoms fraction from the isostripper. The two streams can be passed in indirect heat exchange relationship with a feed stream to one of the the towers in the alkylation system in order to preheat said feed stream. In one embodiment of the invention, the vapor side draw stream from the prefractionation zone and the bottoms fraction from the isostripper are passed, independently, in indirect heat exchange relationship with the feed stream to the prefractionation zone thereby preheating the feed stream. The vapor side draw stream is passed in heat exchange relationship with a feed stream after it has been passed in heat exchange relationship with the isostripper and is being recycled to alkylation. Upon passing the isostripper bottoms in heat exchange relationship with a feed stream, the bottoms stream is then passed to further use or to storage as alkylate product.

In another embodiment of the invention, the amount of heat required by the isostripper can be reduced by flashing the bottoms fraction from the prefractionation zone. The flashed vapor is then recycled to alkylation with the resulting liquid being charged to the isostripper as feed. Normally, the bottoms fraction from the prefractionation zone is charged in its entirety to the isostripper as feed, however, the flashing allows for the removal of some isoparaffin thereby reducing the amount of feed to the isostripper. Also reduced is the amount of heat necessary or required by the isostripper and that the percentage of isoparaffin removed in the flashed vapor does not require heat from the isostripper in order to vaporize it and thereby remove it as overhead for recycle to alkylation.

The process of the invention is applicable to any olefin which can be appropriately used in an alkylation reaction and the particular olefin used will depend upon the type of alkylate product desired. Examples of appropriate olefins are the $C_3$–$C_7$ olefins. The preferred olefins, however, are the propylene and butylenes.

The process of the invention is also applicable to any isoparaffin appropriate for alkylation with the particular isoparaffin to be used depending on the type of alkylate product desired. Examples of appropriate isoparaffins are the $C_4$–$C_8$ isoparaffins with isobutane being the preferred isoparaffin reactant.

The invention is not dependent upon specific reaction conditions as appropriate conditions are conventional and well known in the art. However, the mole ratio of isoparaffin to olefin is usually maintained somewhere in the range of about 4:1 to about 20:1. The volume ratio of acid catalyst to hydrocarbon feed can be maintained at about 4:1, but can be varied in the range of about 0.5:1 to 6:1. The particular temperature at which the reaction is run will depend upon the particular olefin used in the alkylation. Sufficient pressure is used to maintain liquid phases.

Various types of catalysts can be utilized in the process with sulfuric acid, hydrofluoric acid, phosphoric acid, certain halosulfonic acids, and aluminum chloride being examples of appropriate catalysts. Acid acting or acid alkylation catalysts are the more commonly used catalysts hydrofluoric acid being the preferred catalyst because of the relative ease with which it can be regenerated and reused and because of the superior quality of the alkylate that is produced.

Accordingly, one of the preferred embodiments of the invention involves the contacting of an olefin stream of propylene and butylenes with isobutane in the presence of an HF alkylation catalyst. The alkylation effluent is then passed to an HF alkylation phase separator in order to allow the effluent to separate into a hydrocarbon phase and an HF catalyst phase. The hydrocarbon liquid phase from the HF alkylation phase separator is then pumped, indirectly heated, and charged to a high pressure prefractionator. Overhead vapor from the prefractionator is condensed and the yield portion is fed to the depropanizer of a depropanizing-HF stripping operation to yield bottoms liquid propane from the stripper and to yield from the depropanizer a bottoms liquid isobutane which is recycled to alkylation. Bottoms liquid from the prefractionator is charged to a low pressure isostripper. A high temperature vapor side draw from the prefractionator indirectly reboils the mid-portion of the isostripper, then indirectly preheats the prefractionator feed, is further cooled, and then recycled to alkylation. Bottoms alkylate liquid from the isostripper can be used to further indirectly heat the feed to the prefractionator before being passed to storage for further use.

A better understanding of the invention will be obtained upon reference to the following description of the drawing. The following description and disclosed embodiments of the invention are not intended to limit the invention in any way, however, and are only given for illustration.

Referring to the FIGURE, an alkylation process is shown wherein liquid olefin feed and liquid isobutane feed (11) along with subsequently recovered recycle isobutane (12) and cooled system recycled HF catalyst (9) are charged to reactor (10) to produce alkylate gasoline. The particular type of reactor is not important and the various appropriate reactors are well known in the art. The preferred reactor, however, is the riser-reactor as disclosed in U.S. Pat. No. 3,213,157. The reaction emulsion from (10) passes to phase separation (13), the separated lower liquid HF catalyst phase being recycled (9) via cooler (14) to reactor (10), and the hydrocarbon phase being passed by indirect heating means (16) and (17) to prefractionator (20) by means of conduit (21). Overhead yield (22) from tower (20) is indirectly heated at (62) and charged to depropanizer (30). Overhead (61) from depropanizer accumulator (32) is charged to HF stripper (40). Separated HF (33) from accumulator (32) and HF also from (33') is returned (not shown) to alkylation (10). Overhead (41) from HF stripper (40) is charged via condenser (43) to accumulator (32) along with overhead (44) from depropanizer (30). Product propane, after treating, is recovered at (42).

Bottoms (25) from prefractionator (20) is charged to isostripper (50). In one embodiment of the invention, bottoms (25) from (20) can be flashed, at (102) with the remaining liquid (100) being charged to isostripper (50) and the flashed vapors (101) being condensed and added to the overhead from tower (50), as shown. The overhead and flashed vapor are then recycled together.

Overhead from tower (50) is pumped via (51) to line (12) as recycled isobutane. Bottoms (52) from tower (50) can be passed to storage or used to indirectly heat at (17) the feed (21) to tower (20). Stream (52) is then further cooled and recovered as alkylate product. In some operations, normal butane vapor is removed at (55). If this is not done, the stream (52) is conventionally denormal-butanized, not shown, yielding isopentanes and heavies as the alkylate product.

A side draw vapor stream (23) from tower (20) is used to heat interheater (56). The location of the interheater, used to heat the isostripper, is located below feed (25) and above inlet from fired reboiler. In this embodiment, the interheater is located at a mid-locus in isostripper (50). The partially cooled stream (24) from interheater (56) is cooled at (16), in heating indirectly feed to tower (20), and is further cooled and added as liquid to the recycled isobutane (12).

Bottoms (31) from depropanizer (30) are cooled by indirectly heating at (62) the feed (22) to depropanizer (30). The stream (31) is further cooled and condensed and also added to (12) as recycled isobutane.

A calculated example is herewith given in order to illustrate one set of possible operating conditions in accordance with the invention.

| Calculated Operation | | | |
|---|---|---|---|
| I. Operating Conditions (Specific Operation): | | | |
| (10) | HF Alkylation Reactor: | | |
| | Pressure, psig., | | 115 |
| | Temperature, °F., | | 90 |
| | HF/Total H/C vol. ratio | | 4:1 |
| | IC$_4$/olefin mol. ratio | | 20:1 |
| (20) | Prefractionator: | | |
| | Top Zone: | | |
| | Pressure, psig., | | 230 |
| | Temperature, °F., | | 155 |
| | Side Draw: | | |
| | Temperature, °F., | | 200 |
| | Bottom Zone: | | |
| | Pressure, psig., | | 235 |
| | Temperature, °F., | | 210 |
| (30) | Depropanizer: | | |
| | Top Zone: | | |
| | Pressure, psig., | | 240 |
| | Temperature, °F., | | 116 |
| | Bottom Zone: | | |
| | Pressure, psig., | | 245 |
| | Temperature, °F., | | 200 |
| (40) | HF Stripper: | | |
| | Top Zone: | | |
| | Pressure, psig., | | 270 |
| | Temperature, °F., | | 125 |
| | Bottom Zone: | | |
| | Pressure, psig., | | 272 |
| | Temperature, °F., | | 135 |
| (50) | Isostripper: | | |
| | Top Zone: | | |
| | Pressure, psig., | | 90 |
| | Temperature, °F., | | 142 |
| | Mid-Zone: | | |
| | Pressure, psig., | | 92 |
| | Temperature, °F., | | 150 |
| | Bottom Zone: | | |
| | Pressure, psig., | | 95 |
| | Temperture, °F., | | 325 |
| II. Flow Rates (Specific Operation): | | | |
| (11) | Feed Olefins & Isobutane, B/H | | 543 |
| | Composition (of blend), | Vol. % | |
| | Propane | 2.7 | |
| | Isobutane | 50.2 | |
| | Normal Butane | 4.0 | |
| | Butylenes | 43.1 | |
| | Total | 100.0 | |
| (12) | Recycle Isobutane, B/H, | | 4,674 |
| | Composition, | Vol. % | |
| | Propane | 1.1 | |
| | Isobutane | 94.3 | |
| | Normal Butane (plus) | 4.6 | |
| (21) | Feed to Prefractionator, B/H | | 5,196 |
| (22) | Feed to Depropanizer, B/H | | 404 |
| (23) | Vapor Sidedraw (measured as liquid), B/H | | 1,553 |
| | Temperature, °F., | | 200 |
| | Pressure, psig., | | 232 |
| | Vol. % iC$_4$, | | 93 |
| (24) | Cooled return of sidedraw, B/H | | 1,553 |
| | Temperature, °F., | | 95 |
| | Pressure, psig., | | 220 |
| (25) | Bottoms from Prefractionator, B/H | | 3,214 |
| (51) | Isostripper Overhead, B/H | | 2,805 |
| | Vol. % iC$_4$ 94 | | |
| (52) | Alkylate Yield (contains nC$_4$), B/H | | 409 |
| | RON clear of DC$_4$ alkylate 98 | | |
| (41) | Propane Yield, B/H | | 15 |
| (31) | Depropanizer Bottoms, B/H | | 389 |
| | Vol. % iC$_4$ 95 | | |

The liquid hydrocarbon phase from the HF alkylation settler is pressured by the pump to the high pressure prefractionator (20) which is reboiled, for example, with low pressure steam. A vapor side draw, containing "waste heat", and rich in isobutane is removed from the prefractionator and is used to indirectly heat the midportion of the isostripper. This is the main source of heat for the isostripper.

By operating the prefractionator at a relatively high pressure and thereby recovering the side draw vapor at relatively high temperature, and using this vapor as the main heat source for the low pressure isostripper, about 1,500,000,000 Btu/day can be saved as compared with use of low pressure prefractionation and low pressure isostripper. This is equivalent to a savings of $3,750/day using natural gas at $2.50/1000 SCF (Btu of 1,000/SCF of gas). Less fired reboiling of the isostripper is required by the system of the invention than in the prior operation. The prefractionator is preferably operated in the range of about 70 to 200 psi, above the pressure in the isostripper, allowing, thereby, sufficient temperature in the prefractionator side draw and bottoms stream to effect desired interheating and feed temperature for the isostripper; the prefractionation is preferably operated in the range of about 175 to about 300 psig, and at a temperature (depending on alkylate effluent composition) to effect vaporization to produce overhead yield and side draw of about 30 to about 50 volume percent of the feed to the prefractionator.

Reasonable variations and modifications which will become apparent to those skilled in the art can be made in the present invention without departing from the spirit and scope thereof.

I claim:

1. An alkylation process comprising the steps of:
   contacting an olefin and isoparaffin with an acid alkylation catalyst under alkylation conditions to form an alkylate-containing alkylation effluent,
   passing said effluent to a phase separation zone and settling said effluent into a hydrocarbon phase and an acid catalyst phase,
   passing said hydrocarbon phase to a prefractionation zone wherein the hydrocarbon phase is separated into at least three fractions with one fraction being an overhead vapor fraction, another being a bottoms liquid fraction, and the third being a side draw vapor stream, changing said bottom liquid fraction to an isostripper, and passing said side draw vapor stream from the prefractionation zone in indirect heat exchange relationship with the interheater of said isostripper to thereby provide the majority of heat energy required for the isostripper.

2. A process in accordance with claim 1 further comprising the steps of:
charging said overhead fraction from the prefractionation zone to a depropanizer, and
recycling the side draw vapor stream after being passed in indirect heat exchange relationship with the isostripper to said contacting.

3. A process in accordance with claim 2 wherein
said prefractionation zone is a high pressure fractionation zone and
said stripping zone is a low pressure isostripper.

4. A process in accordance with claim 3 wherein the vapor side draw from the prefractionation zone and a bottoms fraction from the isostripper are passed in indirect heat exchange relationship with the feed stream to the prefractionation zone thereby heating said feed stream.

5. A process in accordance with claim 3 wherein a portion of said bottoms fraction from the prefractionation zone is flashed and the flashed vapor is being recycled to said contacting and the remaining liquid after said flashing is being charged to the isostripper as feed.

6. A process in accordance with claim 1 wherein said acid alkylation catalyst is hydrofluoric acid and said isoparaffin is isobutane.

* * * * *